(12) United States Patent
Sugiyama

(10) Patent No.: US 10,244,959 B2
(45) Date of Patent: Apr. 2, 2019

(54) VITAL INFORMATION MEASUREMENT DEVICE AND VEHICLE SEAT

(71) Applicant: TS TECH CO., LTD., Asaka-shi, Saitama (JP)

(72) Inventor: Shinji Sugiyama, Tochigi (JP)

(73) Assignee: TS Tech Co., Ltd., Saitama (JP)

( * ) Notice: Subject to any disclaimer, the term of this patent is extended or adjusted under 35 U.S.C. 154(b) by 449 days.

(21) Appl. No.: 14/891,214

(22) PCT Filed: May 16, 2014

(86) PCT No.: PCT/JP2014/063114
§ 371 (c)(1),
(2) Date: Nov. 13, 2015

(87) PCT Pub. No.: WO2014/185532
PCT Pub. Date: Nov. 20, 2014

(65) Prior Publication Data
US 2016/0089084 A1    Mar. 31, 2016

(30) Foreign Application Priority Data

May 17, 2013    (JP) .................................. 2013-105416

(51) Int. Cl.
*A61B 5/0408*    (2006.01)
*A61B 5/18*    (2006.01)
(Continued)

(52) U.S. Cl.
CPC .......... *A61B 5/0408* (2013.01); *A61B 5/0245* (2013.01); *A61B 5/04085* (2013.01);
(Continued)

(58) Field of Classification Search
CPC .. A61B 5/0408; A61B 5/04085; A61B 5/6893
See application file for complete search history.

(56) References Cited

U.S. PATENT DOCUMENTS 6,532,379 B2 * 3/2003 Stratbucker ........ A61B 5/04085
600/382
8,738,112 B2 * 5/2014 Choe .................. A61B 5/04085
600/391

(Continued)

FOREIGN PATENT DOCUMENTS

DE    20 2012 001 096 U1    3/2012
EP        2 532 306 A1      12/2012
(Continued)

OTHER PUBLICATIONS

Extended European Search Report issued in related application EP 14798097.3, dated Apr. 4, 2016, 11 pages.

(Continued)

*Primary Examiner* — Lee S Cohen
(74) *Attorney, Agent, or Firm* — Drinker Biddle & Reath LLP

(57) ABSTRACT

A vital information measurement device and a vehicle seat which improves the durability of sheet-shaped sensors configured to detect vital information of a seated passenger can stably measure the heart rate of the seated passenger. A vehicle seat includes sheet-shaped sensors attached to a seat back, and can measure the heart rate of a seated passenger based on vital signals of the seated passenger detected by the sheet-shaped sensors. At each sheet-shaped sensor, a sensor overlap reduction section is provided to reduce partial overlapping of the sheet-shaped sensor when the seated passenger leans on the seat back. Specifically, each sheet-shaped sensor includes a first cutout extending toward the center of the sheet-shaped sensor at an outer peripheral portion of the sheet-shaped sensor, and a second cutout formed continuously from the first cutout and extending opposite to the center along the outer peripheral portion of the sheet-shaped sensor.

10 Claims, 11 Drawing Sheets

(51) Int. Cl.
*B60N 2/00* (2006.01)
*A61B 5/0245* (2006.01)
*A61B 5/00* (2006.01)
*A61B 5/024* (2006.01)

(52) U.S. Cl.
CPC .............. *A61B 5/18* (2013.01); *A61B 5/6893* (2013.01); *B60N 2/002* (2013.01); *A61B 5/02444* (2013.01); *A61B 5/6891* (2013.01); *A61B 2503/40* (2013.01); *A61B 2562/0214* (2013.01); *A61B 2562/04* (2013.01); *A61B 2562/164* (2013.01); *A61B 2562/222* (2013.01)

(56) References Cited

U.S. PATENT DOCUMENTS

| 2001/0027270 | A1 | 10/2001 | Stratbucker | |
|---|---|---|---|---|
| 2010/0049608 | A1* | 2/2010 | Grossman | G06Q 30/02 705/14.55 |
| 2015/0133804 | A1* | 5/2015 | Sugiyama | A61B 5/0408 600/509 |

FOREIGN PATENT DOCUMENTS

| EP | 2 839 779 | A1 | 2/2015 |
|---|---|---|---|
| JP | H09-271467 | A | 10/1997 |
| JP | 2001-260698 | A | 9/2001 |
| JP | 2006-231020 | A | 9/2006 |
| JP | 2007-054606 | A | 3/2007 |
| JP | 2007-301175 | A | 11/2007 |
| JP | 2009-050679 | A | 3/2009 |
| JP | 2011-030869 | A | 2/2011 |
| NO | 2010/119441 | A2 | 10/2010 |
| WO | WO 2013/157608 | A1 | 10/2013 |
| WO | 2015/034065 | A1 | 3/2015 |

OTHER PUBLICATIONS

Office Action issued in related application JP 2015-517148, dated Aug. 14, 2018, with machine generated English language translation, 6 pages.

* cited by examiner

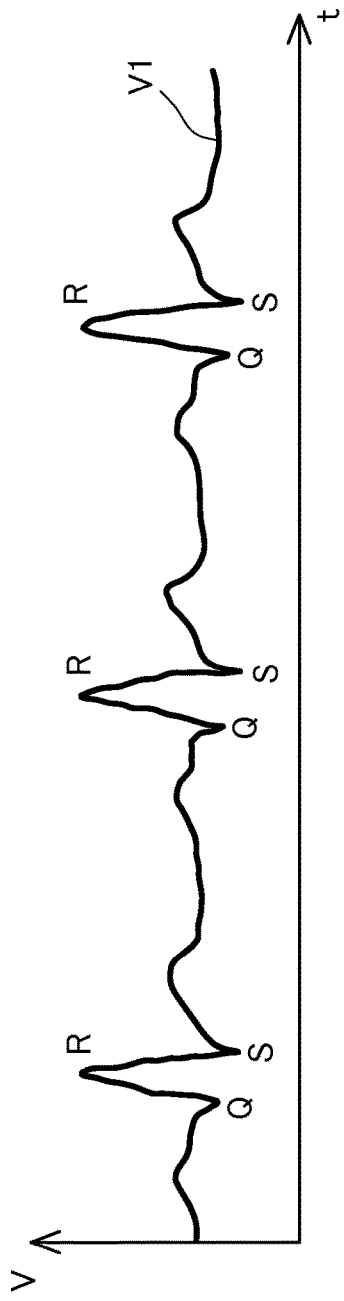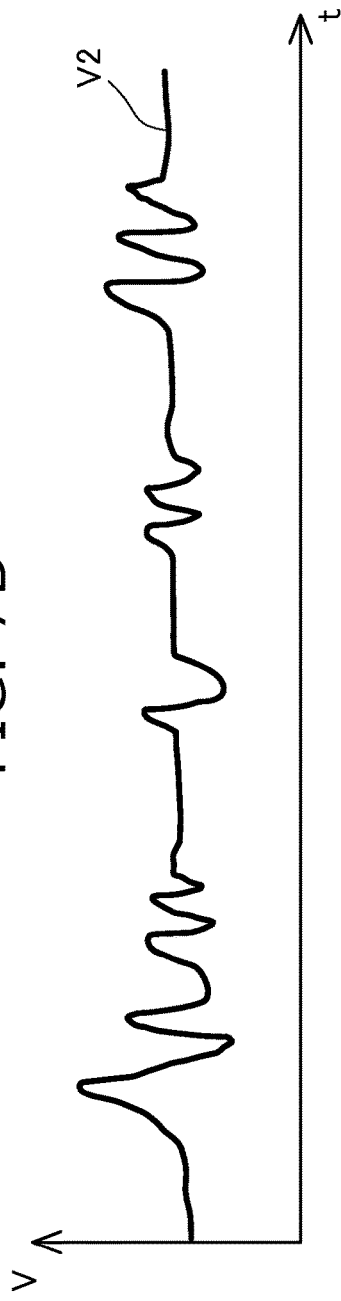

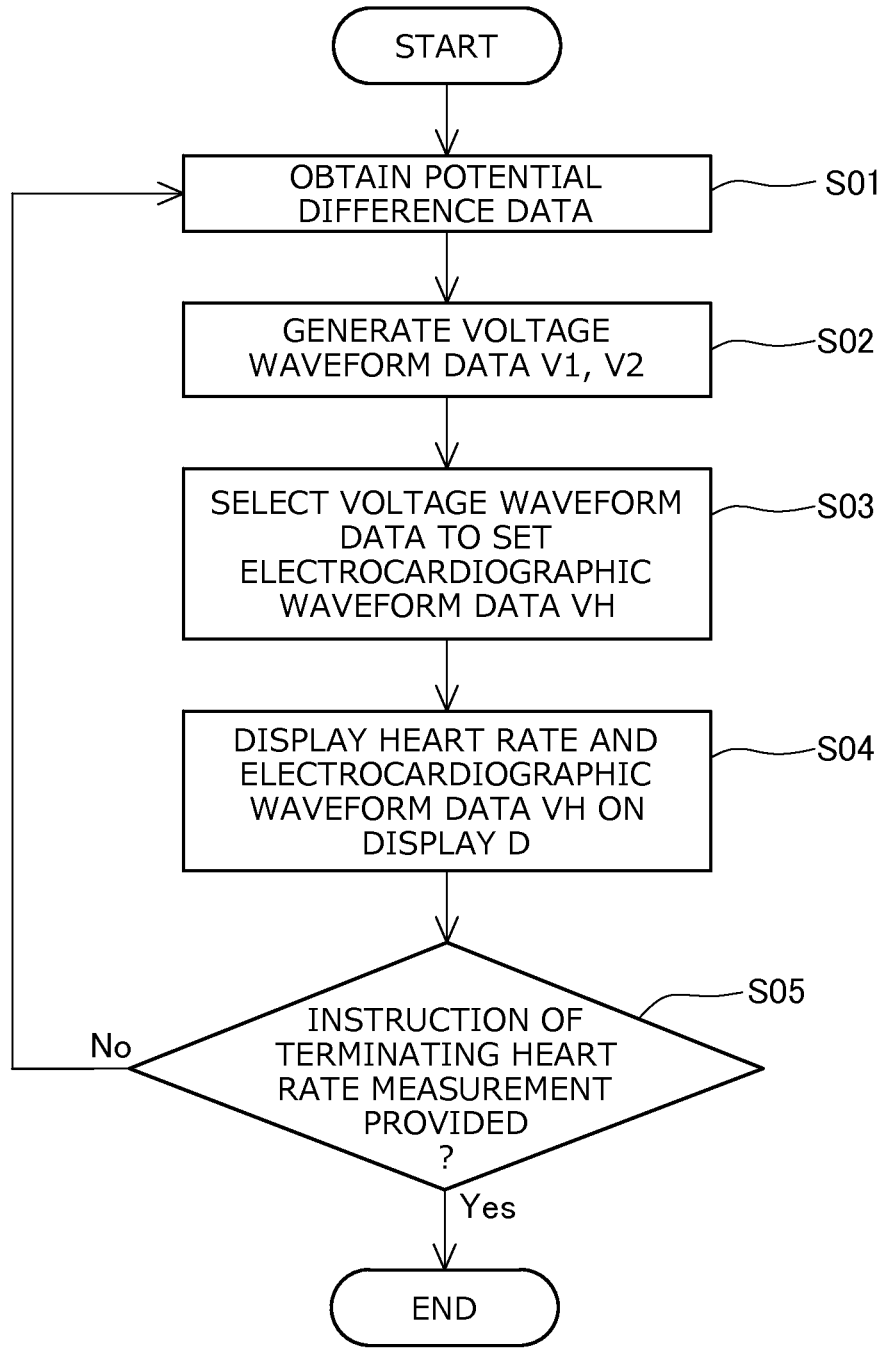

VITAL INFORMATION MEASUREMENT DEVICE AND VEHICLE SEAT

CROSS REFERENCE TO RELATED APPLICATIONS

This application is a National Stage Entry application of PCT Application No. PCT/JP2014/063114, filed May 16, 2014, which claims the priority benefit of Japanese Patent Application No. 2013-105416, filed May 17, 2013, the contents being incorporated herein by reference.

BACKGROUND

Disclosed herein is a vital information measurement device and a vehicle seat, and particularly, a vital information measurement device having the function of measuring vital information of a subject, which may be a human or an animal, and a related vehicle seat.

In recent years, for the purpose of promptly reporting, to a driver, that a driver's physical condition is changed while a vehicle is running, various vehicle seats configured to be able to display a change in physical condition by detecting various parameters indicating the state of the driver have been proposed.

For example, Japanese Patent Document No. 2009-50679 A ("the '679 Document") discloses an electrocardiogram measurement device including first and second electrodes serving as two sensors optionally arranged at a seat back and a ground electrode disposed in a seat cushion and configured to determine a reference potential.

In this electrocardiogram measurement device, an electric signal associated with an electrocardiogram detected from a driver by two sensors is efficiently sensed in such a manner that the electric signal is amplified by a two-stage amplifier, and therefore, the health condition of the driver can be determined.

Japanese Patent Document No. 2007-301175 A ("the '175 Document") discloses a measurement device including planar electrodes serving as a plurality of sensors arranged respectively at the positions contacting the back of a driver, the region extending from the waist to the hip of the driver, and the thighs of the driver.

In this measurement device, one of the sensors is provided for obtaining the neutral-point potential of an amplifier. This reduces signal noise, and therefore, abnormality can be determined in such a manner that a heart-rate signal and a respiration signal from the driver are suitably detected.

Sheet-shaped sensors are broadly used as the sensors of the above-cited references. Each sensor mainly includes a conductive line configuring a sensor body, and a conductive sheet fixing the conductive line. These sensors are arranged in a part of the seat back supporting the back of the seated passenger.

The sheet-shaped sensor of this type might receive a compressive load when the seated passenger leans on the seat back, resulting in wrinkling caused due to partial overlapping of the sheet-shaped sensor. As a result, there is a possibility that signal noise is caused or that the conductive line deforms due to repeat load application.

However, in the vehicle seat including the vital information measurement device as described in the above-cited references, reduction in occurrence of wrinkling of the sheet-shaped sensors has not been taken into consideration.

For this reason, vehicle seats have been demanded which include sheet-shaped sensors which can stably detect vital signals from seated passengers/subjects and which improves durability against repeat load application.

SUMMARY

Various embodiments of the present invention, discussed below, have been made in view of the above-described problem, and provide a vital information measurement device which improves the durability of sheet-shaped sensors configured to detect vital signals from an subject and which can stably measure vital information of the subject, and provide a related vehicle seat.

In particular, these embodiments provide a vital information measurement device which improves the durability of sheet-shaped sensors configured to detect electric signals associated with the biopotential of a seated passenger and which can stably measure the heart rate of the seated passenger, and provide a related vehicle seat.

According to the vital information measurement device described herein, the above-described problem is solved by a vital information measurement device including a sheet-shaped sensor that is configured to detect a vital signal of an subject, wherein the vital information measurement device can measure vital information of the subject based on the vital signal detected by the sheet-shaped sensor, and a sensor overlap reduction section configured to reduce partial overlapping of the sheet-shaped sensor when the subject directly or indirectly contacts the sheet-shaped sensor is provided in at least one of the sheet-shaped sensor or an attachment body to which the sheet-shaped sensor is attached.

As described above, the sensor overlap reduction section configured to reduce partial overlapping of the sheet-shaped sensor when the subject contacts the sheet-shaped sensor is provided in at least one of the sheet-shaped sensor or the attachment body. Thus, the vital information measurement device can be provided, which improves the durability of the sheet-shaped sensor configured to detect the vital signal of the subject and which can stably measure the vital information of the subject.

Specifically, even if the sheet-shaped sensor mainly including the conductive line configuring the sensor body and the conductive sheet fixing the conductive line receives the compressive load from the subject, deformation of the conductive line is reduced by the sensor overlap reduction section. As a result, the durability of the sheet-shaped sensor is improved, and occurrence of signal noise is reduced by reduction in overlapping of the sheet-shaped sensor.

In the above-described state, the sheet-shaped sensor may detect, as the vital signal, an electric signal associated with the biopotential of the subject, and the heart rate (the vital information) of the subject may be measureable based on the electric signal detected by the sheet-shaped sensor.

With the above-described configuration, the device can be provided, which improves the durability of the sheet-shaped sensor configured to detect the electric signal associated with the biopotential of the subject and which can stably measure the heart rate of the subject.

In the above-described state, an opening or a cutout may be, as the sensor overlap reduction section, formed in at least part of the sheet-shaped sensor.

At least one or more of cutouts may be, as the sensor overlap reduction section, formed in an outer peripheral portion of the sheet-shaped sensor.

With the above-described configuration, when the subject contacts the sheet-shaped sensor, the sheet-shaped sensor easily follows elastic deformation of the sheet-shaped sensor itself and elastic deformation of the attachment body. As a result, the durability of the sheet-shaped sensor against repeat load application is improved.

In the above-described state, the cutout may include a first cutout extending toward the center of the sheet-shaped sensor at the outer peripheral portion of the sheet-shaped sensor, and a second cutout formed continuously from the first cutout and extending opposite to the center along the outer peripheral portion of the sheet-shaped sensor.

With the above-described configuration, the sheet-shaped sensor more easily follows elastic deformation of the sheet-shaped sensor itself and elastic deformation of the attachment body. As a result, the durability of the sheet-shaped sensor is further improved.

In the above-described state, the sheet-shaped sensor may at least include a conductive line configuring a sensor body, and a conductive sheet fixing the conductive line, and the conductive line may be disposed along an outer peripheral portion of the conductive sheet.

With the above-described configuration, the sensor overlap reduction section provided in the outer peripheral portion of the conductive sheet reduces deformation of the conductive line disposed along the outer peripheral portion. As a result, the durability of the sheet-shaped sensor is improved, and occurrence of signal noise is reduced.

In the above-described state, the attachment body may be a seat back serving as a backrest of a vehicle seat on which the subject is seated. The sheet-shaped sensor may be disposed in part of the seat back supporting the back of the subject. The sheet-shaped sensor may include a first sensor and a second sensor disposed on the right side of the first sensor as viewed from the seated human or the seated animal.

The second sensor may be disposed opposite to the first sensor in the vertical direction, and protrudes above the first sensor.

With the above-described configuration, when the seated human or the seated animal leans on the seat back, the sheet-shaped sensor easily follows elastic deformation of the cushion pad configuring the seat back. As a result, the durability of the sheet-shaped sensor against repeat load application is improved.

Moreover, with the above-described configuration, the sheet-shaped sensor easily and stably detects a great potential difference signal generated in association with contraction of a heart of the seated human or the seated animal.

Specifically, a heart-induced electric vector produced when the heart of a person expands/contracts typically points in the direction substantially from the right shoulder to the left leg. Such a direction corresponds to the direction from the upper right side to the lower left side as viewed from the seated passenger. In this state, since the second sensor disposed on the right side as viewed from the seated passenger protrudes above the first sensor, these sensors are in such arrangement that the direction connecting between the second sensor and the first sensor is along the direction of the heart-induced electric vector. Thus, the sheet-shaped sensor easily and stably detects the potential difference signal generated in associated with contraction of the heart. Moreover, since the vital information can be measured at, for example, a position near the heart, the heart rate information is easily measured.

In the above-described state, the vital information measurement device may include a distribution cable electrically connected to the sheet-shaped sensor and configured to transmit the vital signal detected by the sheet-shaped sensor, and the distribution cable may be disposed outside the first and second sensors in a seat width direction at the seat back.

With the above-described configuration, the distribution cable can be compactly gathered, and therefore, the size of the seat back configuring the vehicle seat can be reduced.

In the above-described state, the distribution cable may be disposed outside the first sensor in the seat width direction at the seat back, and part of the second sensor protruding above the first sensor may extend in the seat width direction, and is electrically connected to the distribution cable.

With the above-described configuration, each of the first and second sensors can be, using a free space, electrically connected to the distribution cable, and the size of the seat back can be reduced.

In the above-described state, the sheet-shaped sensor may include a sensor connection portion connecting the first and second sensors together.

With the above-described configuration, since the first and second sensors form an integrated component, the sheet-shaped sensor is, with high accuracy, easily attached to a pre-set position of the seat back. Moreover, the number of components can be reduced.

In the above-described state, the sheet-shaped sensor may further include a third sensor disposed above the first and second sensors, and a fourth sensor disposed on the right side of the third sensor as viewed from the seated human or the seated animal. The fourth sensor may be disposed opposite to the third sensor in the vertical direction, and may protrude above the third sensor.

With the above-described configuration, the sheet-shaped sensor can stably detect the vital signal regardless of a physique difference among seated passengers.

Specifically, the sheet-shaped sensor is disposed such that the position of the heart of a small seated passenger is within the region surrounded by the first and second sensors, and is disposed such that the position of the heart of a big seated passenger is within the region surrounded by the third and fourth sensors.

Moreover, according to a vehicle seat described herein, the above-described problem is solved in such a manner that the vehicle seat includes the above-described vital information measurement device.

In such a state, the sheet-shaped sensor may be attached to a cushion pad configuring a seat back, a distribution cable electrically connected to the sheet-shaped sensor and configured to transmit the vial signal detected by the sheet-shaped sensor may be provided, and a cable housing recess may be formed in part of the cushion pad opposite to the distribution cable.

With the above-described configuration, the distribution cable can be compactly housed, and therefore, the size of the seat back can be reduced. Moreover, the sense of discomfort is reduced when the seated passenger leans on the seat back.

In the above-described state, the seat back may be configured such that the cushion pad is covered with a skin, a skin insertion groove into which an end of the skin is inserted may be formed in the cushion pad, and the sheet-shaped sensor may be disposed in a position other than part of the cushion pad formed with the skin insertion groove.

Moreover, the sheet-shaped sensor may be disposed along the skin insertion groove.

With the above-described configuration, when the cushion pad to which the sheet-shaped sensor is attached is covered with the skin, the sheet-shaped sensor and the skin insertion groove do not interfere with each other. Thus, the end of the skin can be efficiently inserted into the skin insertion groove.

According to an embodiment of the invention, the sensor overlap reduction section is provided. Thus, the vital information measurement device can be provided, which improves the durability of the sheet-shaped sensor configured to detect the vital signal of the subject and which can stably measure the vital information of the subject.

According to an embodiment of the invention, when the subject contacts the sheet-shaped sensor, the sheet-shaped sensor easily follows elastic deformation of the sheet-shaped sensor itself and elastic deformation of the attachment body. As a result, the durability of the sheet-shaped sensor against repeat load application is improved.

According to an embodiment of the invention, when the seated subject leans on the seat back, the sheet-shaped sensor easily follows elastic deformation of the cushion pad configuring the seat back. As a result, the durability of the sheet-shaped sensor against repeat load application is improved.

Moreover, the sheet-shaped sensor easily and stably detects a great potential difference signal generated in association with contraction of the heart of the seated subject.

According to an embodiment of the invention, the distribution cable can be compactly gathered, and therefore, the size of the seat back configuring the vehicle seat can be reduced.

According to an embodiment of the invention, since the first and second sensors form an integrated component, the sheet-shaped sensor is, with high accuracy, easily attached to the pre-set position of the seat back. Moreover, the number of components can be reduced.

According to an embodiment of the invention, the sheet-shaped sensor can stably detect the vital signal regardless of the physique difference among seated passengers.

According to an embodiment of the invention, the size of the seat back can be reduced. Moreover, the sense of discomfort is reduced when the seated passenger leans on the seat back.

According to an embodiment of the invention, the end of the skin can be efficiently inserted into the skin insertion groove.

BRIEF DESCRIPTION OF DRAWINGS

FIGS. 7A and 7B are graphs showing examples of detected waveform data.

FIG. 8 is a flowchart showing an example of a heart rate measurement process.

DETAILED DESCRIPTION

The present embodiment relates to a vehicle seat which includes sheet-shaped sensors attached to a seat back and which can measure the heart rate of a seated passenger based on vital signals of the seated passenger detected by the sheet-shaped sensors. Each sheet-shaped sensor includes, as a sensor overlap reduction section, a plurality of cutouts at an outer peripheral portion thereof.

Note that the side on which the passenger is seated on the seat back of the vehicle seat is defined herein as a seat front side.

Figure 1:
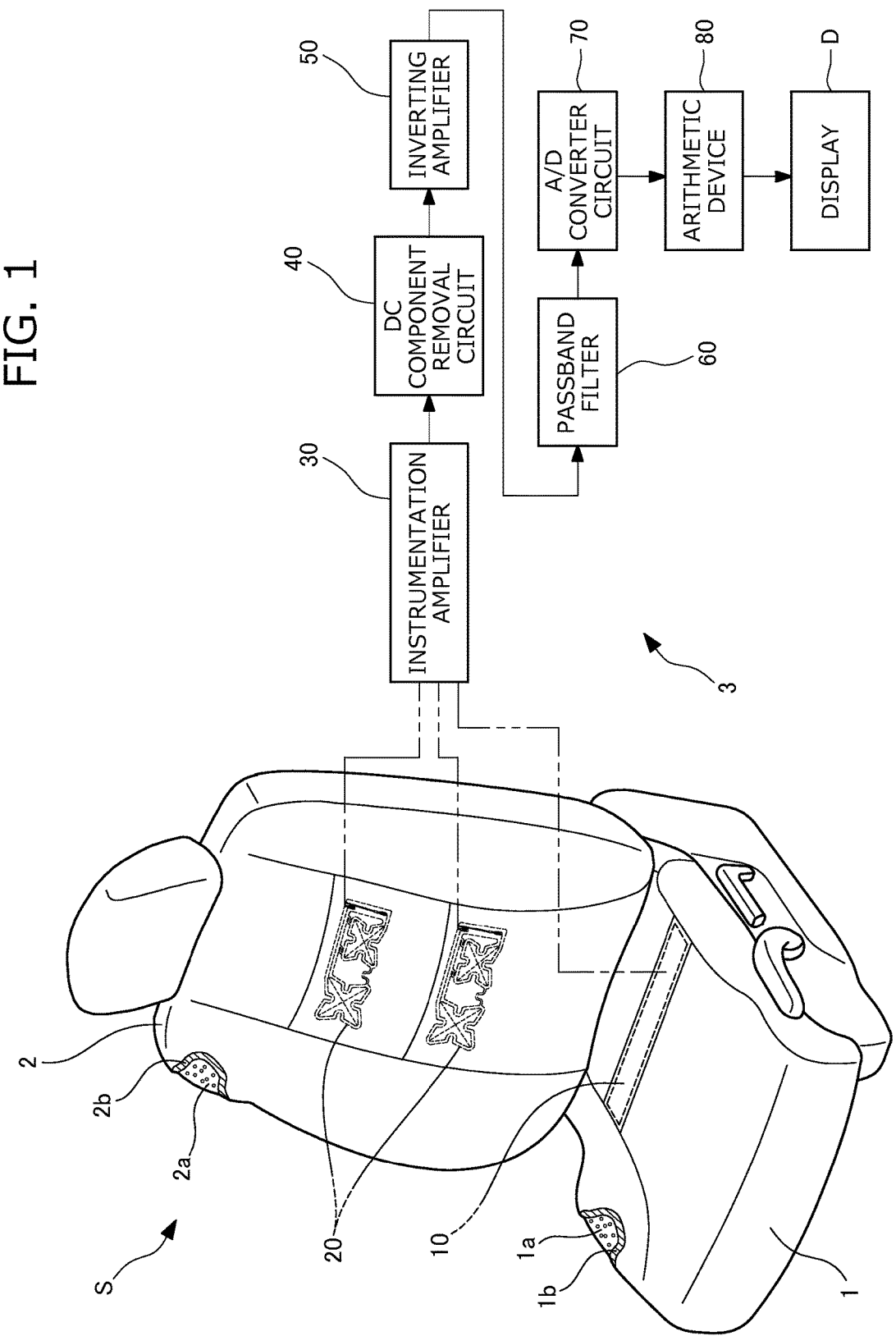
FIG. 1 is a combination perspective-block diagram view illustrating the entire configuration of a vehicle seat of an embodiment of the present invention.

A vehicle seat S of the present embodiment mainly includes, as illustrated in FIG. 1, a seat cushion 1 on which a passenger is seated, a seat back 2 rotatably attached to a back portion of the seat cushion 1 and serving as a backrest of the seated passenger, and a heart rate measurement device 3 including a plurality of sheet-shaped sensors 20 attached inside the seat back 2.

Note that in the embodiments, the seat back 2 is equivalent to an attachment body, and the heart rate measurement device 3 is equivalent to a vital information measurement device.

As illustrated in FIG. 1, the seat cushion 1 is configured such that a cushion pad 1a placed on a not-shown cushion frame configuring a framework is covered with a skin 1b.

A ground electrode 10 is disposed between the cushion pad 1a and the skin 1b at the position facing the hip of the seated passenger.

As illustrated in FIG. 1, the seat back 2 is configured such that a cushion pad 2a placed on a not-shown back frame configuring the framework is covered with a skin 2b.

Figure 2:
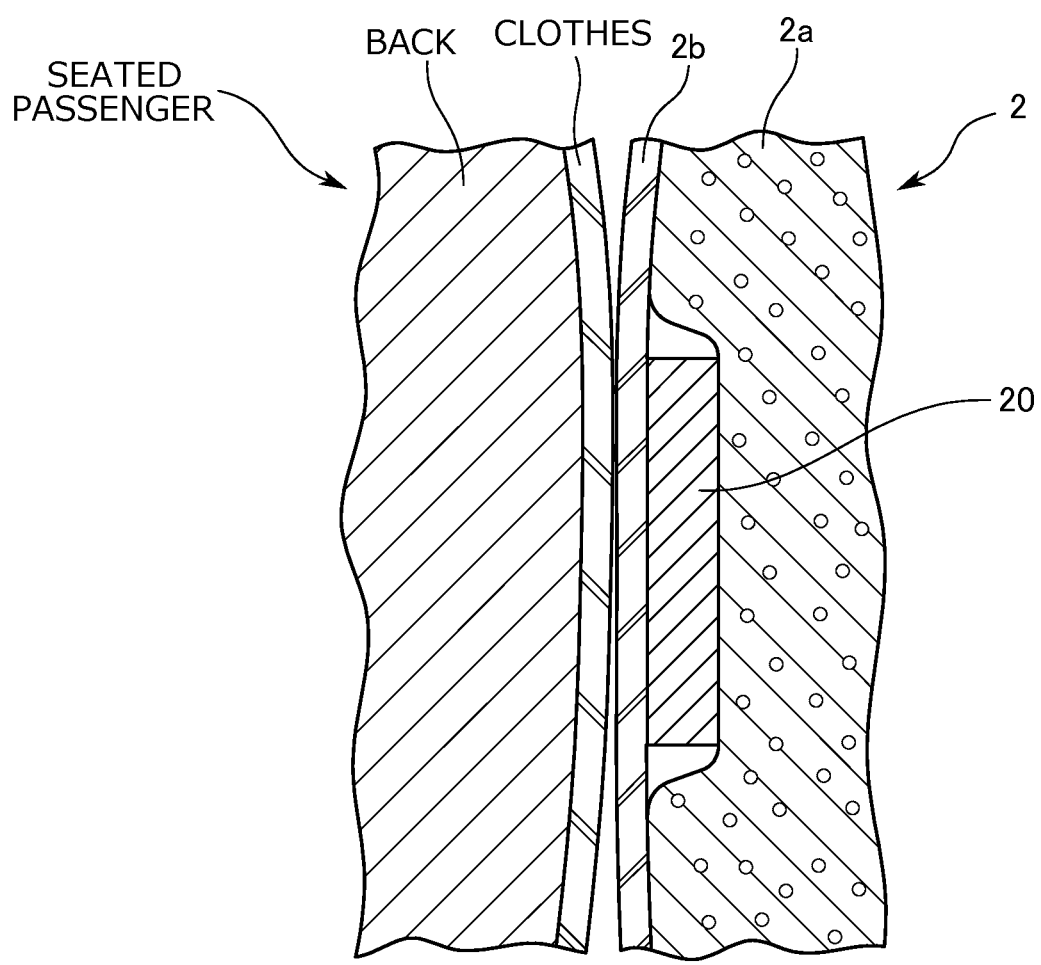
FIG. 2 is a partial longitudinal sectional view of a seat back illustrating arrangement of sheet-shaped sensors.

Moreover, as illustrated in FIG. 2, the sheet-shaped sensors 20 are arranged between the cushion pad 2a and the skin 2b at part of the seat back 2 supporting the back of the seated passenger.

Note that a not-shown cushion slab may be further disposed between the cushion pad 2a and each sheet-shaped sensor 20. This configuration reduces the influence on measurement accuracy and the sense of discomfort when the seated passenger leans on the seat back 2.

The heart rate measurement device 3 is a device configured to detect an electric signal associated with the biopotential of the seated passenger to measure the heart rate of the seated passenger based on the detected electric signal. The heart rate measurement device 3 mainly includes, as illustrated in FIG. 1, the ground electrode 10 provided inside the seat cushion 1, the sheet-shaped sensors 20 provided inside the seat back 2, an instrumentation amplifier 30, a DC component removal circuit 40, an inverting amplifier 50, a passband filter 60, an A/D converter circuit 70, an arithmetic device 80, and a display D.

The ground electrode 10 is formed of a conductive fabric tape, and is configured to obtain a reference potential when an offset signal contained in the electric signal detected by the sheet-shaped sensor 20 is removed. The ground electrode 10 is disposed in part of the seat cushion 1 facing the hip of the seated passenger.

The ground electrode 10 has a function to be capacitance-coupled to the body of the seated passenger via the skin 1b and cloths to detect the electric signal associated with the biopotential of the seated passenger.

Each sheet-shaped sensor 20 is formed of a conductive fabric tape, the conductive fabric tape including a conductive line configuring a sensor body and a conductive sheet for bonding the conductive line. As illustrated in FIG. 2, each sheet-shaped sensor 20 is a sensor configured to be capacitance-coupled to the body of the seated passenger via the skin 2b and the cloths to detect the electric signal associated with the biopotential of the seated passenger.

Figure 3:
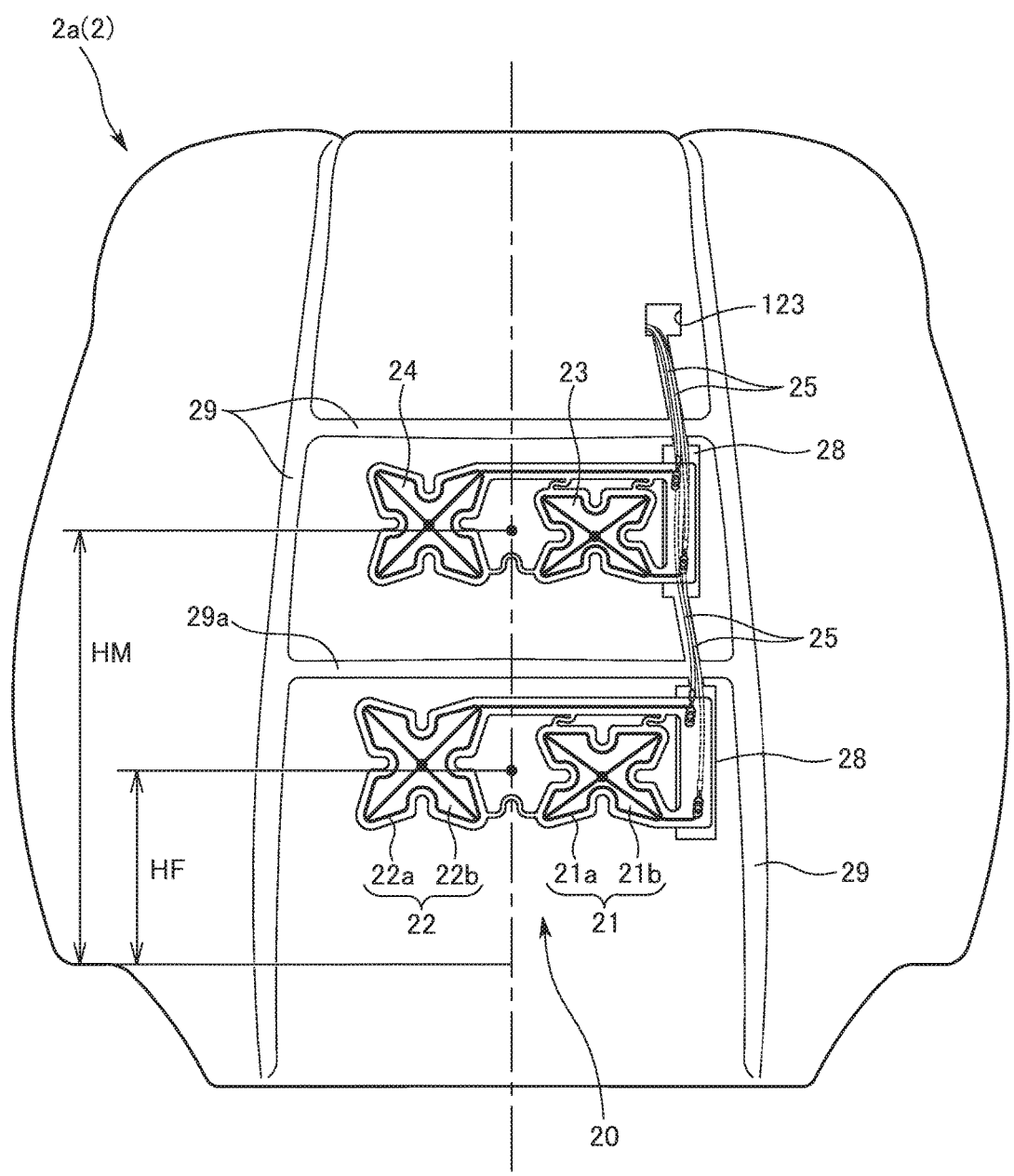
FIG. 3 is a front view of a cushion pad illustrating arrangement of the sheet-shaped sensors.

As illustrated in FIG. 3, each sheet-shaped sensor 20 is bonded to the front side of the cushion pad 2a configuring the seat back 2. The sheet-shaped sensors 20 include a first sensor 21 and a second sensor 22 arranged at the substantially middle of the cushion pad 2a in a seat width direction, and a third sensor 23 and a fourth sensor 24 arranged above the first sensor 21 and the second sensor 22.

The first sensor 21 is in a substantially petal shape, and is disposed in opposite to the second sensor 22 in the vertical direction. The first sensor 21 may have an optional size, and for example, the relationship between the height and the width may be a ratio of about 3:4.

Figure 4:
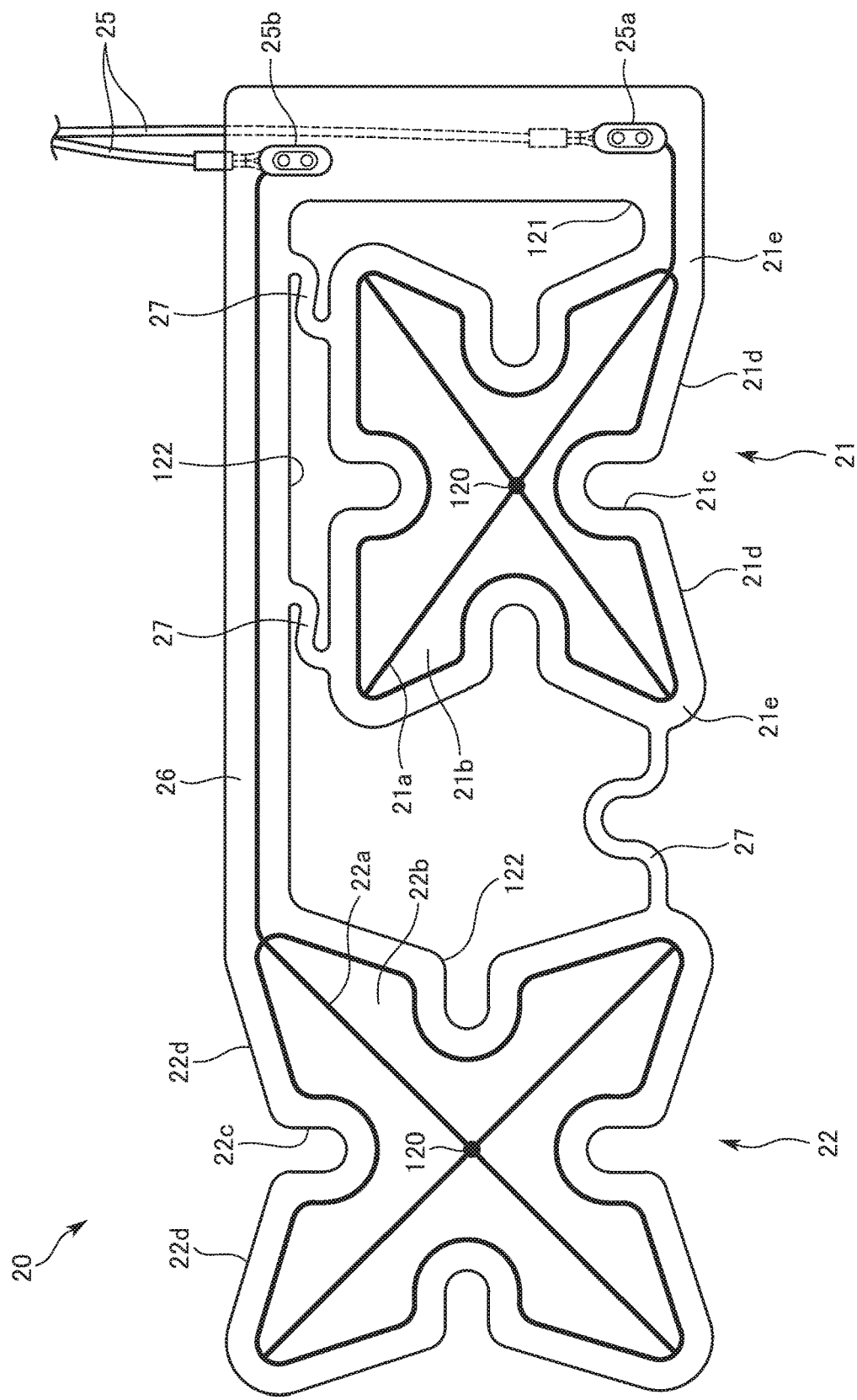
FIG. 4 is a front view illustrating the shape of the sheet-shaped sensors.

As illustrated in FIG. 4, a conductive line 21a configuring the sensor body of the first sensor 21 is formed along an outer peripheral portion (an outer edge portion) of a conductive sheet 21b and along the diagonal lines of the conductive sheet 21b, and is bonded to the outer surface of the conductive sheet 21b.

The conductive sheet 21b includes, as a sensor overlap reduction section, four first cutouts 21c extending toward the center at the outer peripheral portion of the conductive sheet 21b, and three second cutouts 21d each formed continuously from a corresponding one of the first cutouts 21c and extending opposite to the center along the outer peripheral portion of the conductive sheet 21b.

Each first cutout 21c is a cutout in a substantially semi-elliptical shape, and is formed from a corresponding one of the four sides of the conductive sheet 21b toward the center at the outer peripheral portion of the conductive sheet 21b.

Each second cutout 21d is a cutout in a substantially triangular shape. Each second cutout 21d is formed continuously from a corresponding one of three first cutouts 21c other than the first cutout 21c formed in an upper portion of the conductive sheet 21b, and is formed along the outer peripheral portion of the conductive sheet 21b such that the width thereof increases with an increase in the distance from the center.

Specifically, each second cutout 21d extends continuously from a corresponding one of the first cutouts 21c such that the width thereof increases toward ones of corners 21e positioned respectively on opposing sides relative to the corresponding one of the first cutouts 21c, supposing that four corners of the outer peripheral portion of the conductive sheet 21b positioned farthest from the center are the corners 21e.

An optional level of R is provided to the corners 21e and to each corner portion where the first cutout 21c and the second cutout 21d are continuous from each other, and therefore, partial overlapping of the first sensor 21 when the seated passenger leans on the seat back 2 can be reduced.

Note that the total depth of the first cutout 21c and the second cutout 21d may be optionally set, and, for example, is preferably set at equal to or less than about ¼ of the width of the first sensor 21 in the seat width direction.

As illustrated in FIG. 3 or 4, the second sensor 22 is in a substantially petal shape. The second sensor 22 is disposed on the right side of the first sensor 21 as viewed from the seated passenger, and protrudes above the first sensor 21. The second sensor 22 may have an optional size, and for example, the relationship between the height and the width may be a ratio of about 1:1.

As in the first sensor 21, a conductive line 22a configuring the sensor body of the second sensor 22 is formed along an outer peripheral portion of a conductive sheet 22b and along the diagonal lines of the conductive sheet 22b, and is bonded to the outer surface of the conductive sheet 22b.

The conductive sheet 22b includes, as a sensor overlap reduction section, four first cutouts 22c extending toward the center at the outer peripheral portion of the conductive sheet 22b, and four second cutouts 22d each formed continuously from a corresponding one of the first cutouts 22c and extending opposite to the center along the outer peripheral portion of the conductive sheet 22b.

Note that the second cutouts 22d are different from the second cutouts 21d of the first sensor 21 in that each second cutout 22d is formed continuously from a corresponding one of all of four first cutouts 22c.

Moreover, the total depth of the first cutout 22c and the second cutout 22d may be optionally set, and for example, is preferably set at equal to or less than about ¼ of each of the height and width of the second sensor 22 in each of the vertical direction and the seat width direction.

As illustrated in FIG. 3, the first sensor 21 and the second sensor 22 are arranged respectively on opposing sides relative to the center line of the seat back 2 in the seat width direction.

The first sensor 21 and the second sensor 22 are electrically connected respectively to distribution cables 25 disposed outside the first sensor 21 in the seat width direction at the seat back 2.

The distribution cables 25 are cables for transmitting, to the instrumentation amplifier 30, electric vital signals detected by the sheet-shaped sensors 20. As illustrated in FIG. 4, one end 25a of the distribution cable 25 is connected to the conductive line 21a of the first sensor 21 at a lower end portion of the first sensor 21 positioned opposite to the second sensor 22.

Moreover, the other end 25b of the distribution cable 25 is connected to the conductive line 22a of the second sensor 22 at part of the second sensor 22 protruding above the first sensor 21 and positioned close to the first sensor 21.

Specifically, the upwardly-protruding portion of the second sensor 22 positioned close to the first sensor 21 forms a second sensor extension 26 extending horizontally in the seat width direction, and an end portion of the second sensor extension 26 is connected to the end 25b of the distribution cable 25.

The second sensor extension 26 is in a rectangular shape elongated in the seat width direction, and is disposed to extend over the first sensor 21.

The first sensor 21 and the second sensor 22 are connected together via three sensor connection portions 27 to form an integrated component.

Each sensor connection portion 27 is made of a sheet material in a substantially curved shape. One of the sensor connection portions 27 is disposed to connect between a lower end portion of the first sensor 21 positioned close to the second sensor 22 and a lower end portion of the second sensor 22 positioned close to the first sensor 21.

The remaining two sensor connection portions 27 connect between an upper end portion of the first sensor 21 and the second sensor extension 26 of the second sensor 22, and are arranged with a predetermined distance in the seat width direction.

As described above, since the sensor connection portions 27 are in the curved shape, the entirety of the sheet-shaped sensors 20 including the sensor connection portions 27 easily follows elastic deformation of the cushion pad 2a, and therefore, durability is improved.

The shape, arrangement, and configuration of the third sensor 23 and the fourth sensor 24 are the same as those of the first sensor 21 and the second sensor 22. As illustrated in FIG. 3, the third sensor 23 and the fourth sensor 24 are electrically connected respectively to distribution cables 25 disposed outside the third sensor 23 in the seat width direction at the seat back 2.

As illustrated in FIG. 3, a cable housing recess 28 is formed in a front portion of the cushion pad 2a of the seat back 2 in opposite to the distribution cables 25, and a skin insertion groove 29 is formed in part of the cushion pad 2a other than part of the cushion pad 2a to which the sheet-shaped sensors 20 are attached.

The cable housing recess 28 is a housing groove elongated in the vertical direction and having a substantially rectangular cross section, and is formed to have a size sufficient for housing the distribution cables 25.

Note that a through-hole 123 is formed to penetrate, in a seat front-to-back direction, part of the cushion pad 2a positioned above the sheet-shaped sensors 20, and the distribution cables 25 extend from the front side of the cushion pad 2a to pass through the through-hole 123, and then, are connected to the instrumentation amplifier 30 disposed on the back side of the cushion pad 2a.

The skin insertion groove 29 is a groove into which an end of the skin 2b is inserted. The skin insertion groove 29 includes two grooves elongated in the vertical direction and having a substantially rectangular cross section, and two grooves elongated in the seat width direction and having a substantially rectangular cross section. The skin insertion groove 29 is at a position other than the position of the entirety of the sensor bodies of the sheet-shaped sensors 20.

Such an arrangement prevents the sheet-shaped sensors 20 and the skin insertion groove 29 from interfering with each other in the process of inserting the skin end.

A skin insertion groove 29a elongated in the seat width direction is formed in a part of the cushion pad 2a having the greatest thickness in the seat front-to-back direction. The sheet-shaped sensors 20 are arranged to surround and sandwich the skin insertion groove 29a.

Such arrangement of the sheet-shaped sensors 20 easily determine the positions of the sheet-shaped sensors 20, resulting in better assembly.

The height positions of the sheet-shaped sensors 20 attached to the cushion pad 2a will be described with reference to FIGS. 3 and 5.

Figure 5:
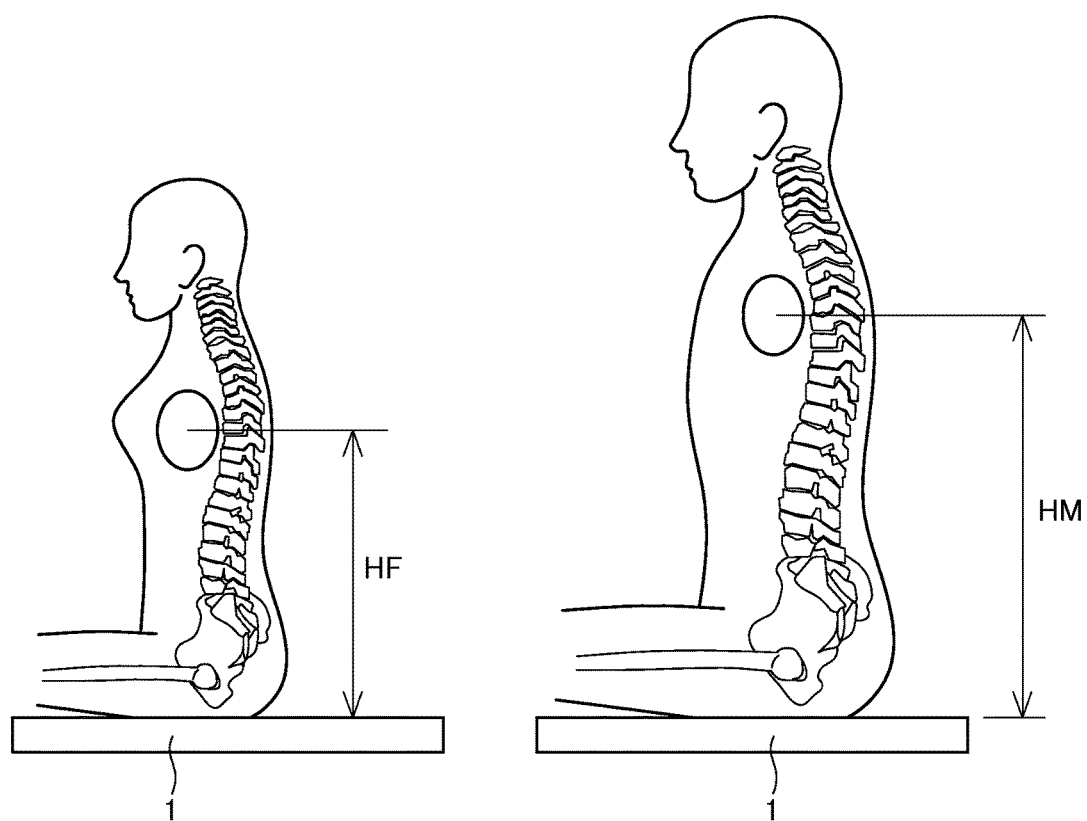
FIG. 5 is a pictorial side view illustrating the difference in the height of the heart due to a physique difference.

First, a physically-small female and a physically-big male are illustrated in FIG. 5 as examples of seated passengers with a physique difference. Suppose that the female assumed as being physically small has a height of about 150 cm, and the male assumed as being physically big has a height of about 190 cm.

When seated on the seat cushion 1, the heart of the female is at a height HF from a cushion seating surface corresponding to the upper surface of the seat cushion 1, and the heart of the male is at a height HM from the cushion seating surface.

For the sheet-shaped sensors 20 attached to the seat back 2, arrangement in a height direction is set depending on a heart position difference caused due to the physique difference.

Specifically, as illustrated in FIG. 3, the first sensor 21 and the second sensor 22 are arranged such that the height of the center between the first sensor 21 and the second sensor 22 from the cushion seating surface corresponds to the height HF of the heart of the female. Moreover, the third sensor 23 and the fourth sensor 24 are arranged such that the height of the center between the third sensor 23 and the fourth sensor 24 from the cushion seating surface corresponds to the height HM of the heart of the male.

Of the sheet-shaped sensors 20 arranged as described above, the left first sensor 21 and the right second sensor 22 as viewed from the seated passenger are arranged to sandwich the heart of the female in an oblique direction. The region defined to include the first sensor 21 at a lower left corner and to include the second sensor 22 at an upper right corner is a region where a suitable potential difference is obtained in detection of the cardiac potential of the female.

Similarly, the left third sensor 23 and the right fourth sensor 24 as viewed from the seated passenger are arranged to sandwich the heart of the male in the oblique direction. The region defined to include the third sensor 23 at a lower left corner and to include the fourth sensor 24 at an upper right corner is a region where a suitable potential difference is obtained in detection of the cardiac potential of the male.

Reasons for such an arrangement will be described below. Typically, the heart-induced electric vector produced in the expansion/contraction of the heart of a person points in the direction substantially from the right shoulder to the left leg. Such a direction corresponds to the direction from the upper right side to the lower left side as viewed from the seated passenger when the passenger is seated on the vehicle seat S. In this state, since the second sensor disposed on the right side as viewed from the seated passenger protrudes above the first sensor, these sensors are arranged such that the direction connecting between the second sensor and the first sensor is along the direction of the heart-induced electric vector. Thus, the sheet-shaped sensors easily and stably detect great potential difference signals generated in associated with contraction of the heart.

Figure 6:
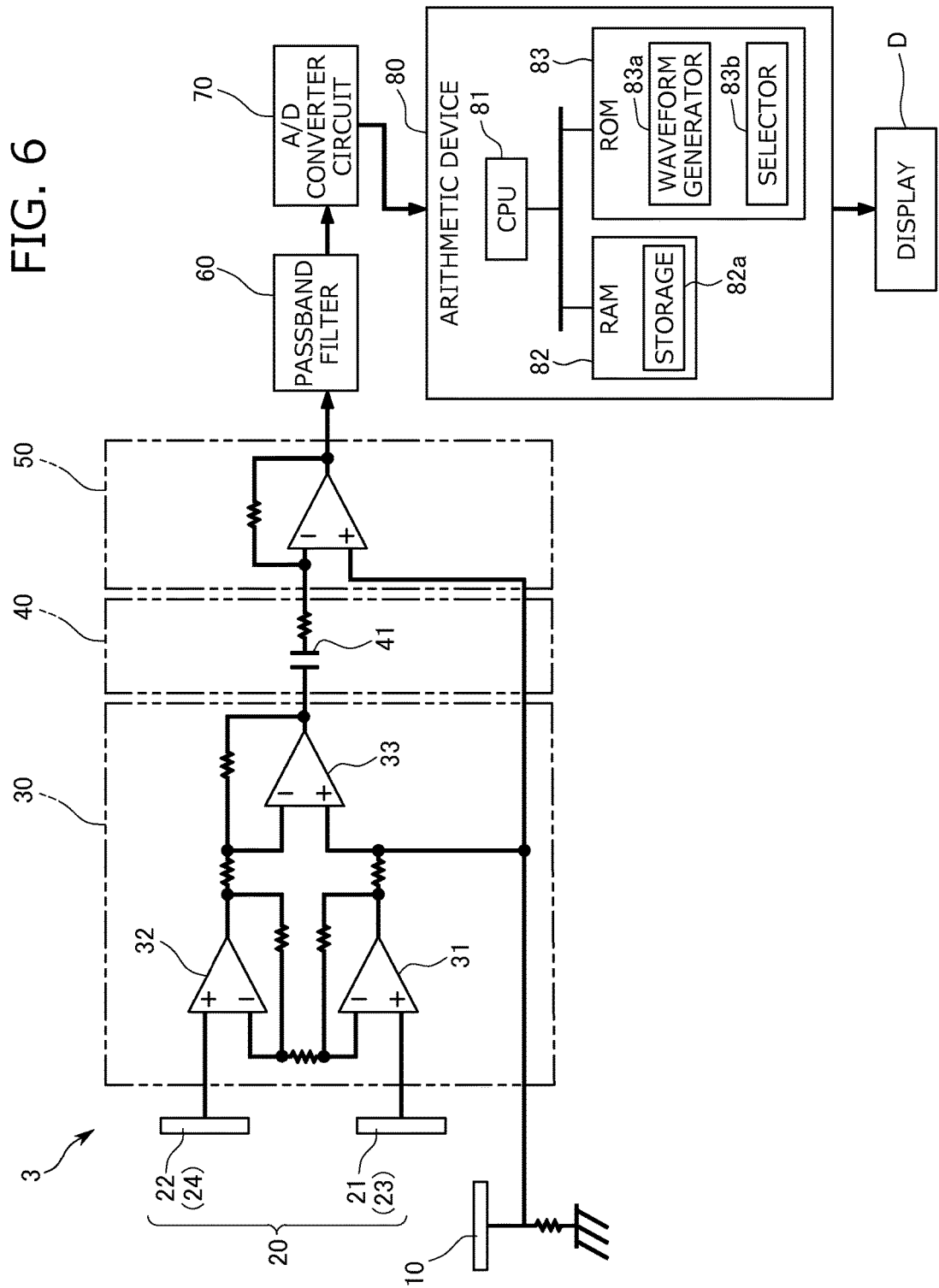
FIG. 6 is a schematic diagram illustrating a circuit configuration and an arithmetic device configuration which are provided for electrocardiographic signal detection.

Next, the instrumentation amplifier 30 includes, as illustrated in FIG. 6, operational amplifiers 31, 32, 33. The operational amplifiers 31, 32 are each configured to amplify electric signals detected by the sheet-shaped sensors 20 to output the signals to the operational amplifier 33.

The operational amplifier 33 is a differential amplifier, and is configured to amplify a difference signal of the electric signals output from the operational amplifiers 31, 32.

The potential of the ground electrode 10 is, as a reference potential, applied to a positive input terminal of the operational amplifier 33. The ground electrode 10 is provided in the seat cushion 1 farther from the heart of the seated passenger than the sheet-shaped sensors 20 provided in the seat back 2, and is capacitance-coupled to the hip of the seated passenger. Thus, the potential less susceptible to the influence of an electrocardiographic signal is obtained from the ground electrode 10.

A capacitor 41 serving as the DC component removal circuit 40 has a function to remove a low-frequency component, including a direct-current component, of the potential difference signal output from the operational amplifier 33, and AC-couples an output terminal of the operational amplifier 33 and a negative input terminal of the inverting amplifier 50 together.

The inverting amplifier 50 has a function to invert, for further amplification, the polarity of the potential difference signal from which the direct-current component is removed. The negative input terminal of the inverting amplifier 50 is connected to the capacitor 41 via a resistor, and the potential of the ground electrode 10 is applied to a positive input terminal of the inverting amplifier 50 as a reference potential.

The passband filter 60 is provided to remove, from the potential difference signal output from the inverting amplifier 50, a low-frequency component and a high-frequency component, these components being not taken as the frequency of the electrocardiographic signal.

The passband filter 60 inputs, in a restrictive manner, the potential difference signal having the frequency of the electrocardiographic signal to the A/D converter circuit 70.

The A/D converter circuit 70 is configured to convert, as an input signal of the arithmetic device 80, an analog signal input from the inverting amplifier 50 via the passband filter 60 into a digital signal.

The arithmetic device 80 includes, for arithmetic control, a CPU 81, a RAM 82, and a ROM 83.

The signal input to the arithmetic device 80 is the potential difference signal converted into the digital signal, and the signal output from the arithmetic device 80 is the electric signal to be displayed on the display D.

The RAM 82 is configured to temporarily store the parameters containing the signal during the arithmetic control and the input and output signals, and has a function as a storage 82a configured to store the potential difference signal converted into the digital signal and other signals.

The ROM 83 is configured to store the program to be executed by the CPU 81 and parameters of predetermined values. The ROM 83 stores, as programs, a waveform generator 83a configured to generate voltage waveform data from the potential difference signal obtained from the sheet-shaped sensors 20 and a selector 83b configured to select voltage waveform data periodically oscillating in association with contraction of the heart.

The waveform generator 83a has a function to generate voltage waveform data V1 based on the potential difference signal, stored in the storage 82a, between the first sensor 21 and the second sensor 22 and a function to generate voltage waveform data V2 based on the potential difference signal between the third sensor 23 and the fourth sensor 24, provided that the vertical axis represents the potential difference signal and the horizontal axis represents the time.

The selector 83b has a function to select, from the voltage waveform data V1, V2, the voltage waveform data associated with contraction of the heart to set such data as electrocardiographic waveform data VH.

Suppose that the voltage waveform data V1 shown in FIG. 7A is generated based on the potential difference signal between the first sensor 21 and the second sensor 22 and that the voltage waveform data V2 shown in FIG. 7B is generated based on the potential difference signal between the third sensor 23 and the fourth sensor 24.

In this case, the selector 83b selects the voltage waveform data V1 clearly showing a periodic R-wave and having a high amplitude to set the voltage waveform data V1 as the electrocardiographic waveform data VH.

Heart Rate Measurement Process

Next, a heart rate measurement method by the heart rate measurement device 3 will be described with reference to FIG. 8.

In response to start of an engine of the vehicle or pressing of a start switch, the sheet-shaped sensors 20 detect electric signals associated with the biopotential of the body of the seated passenger.

The electric signals detected by the first sensor 21 and the second sensor 22 are, as potential difference data, stored in the storage 82a of the arithmetic device 80 via the instrumentation amplifier 30, the DC component removal circuit 40, the inverting amplifier 50, the passband filter 60, and the A/D converter circuit 70. Similarly, the electric signals detected by the third sensor 23 and the fourth sensor 24 are also stored as potential difference data.

That is, the arithmetic device 80 obtains the potential difference data between the first sensor 21 and the second sensor 22 and the potential difference data between the third sensor 23 and the fourth sensor 24 (step S01).

Next, based on the obtained potential difference data between the first sensor 21 and the second sensor 22, the waveform generator 83a generates the voltage waveform data V1 plotted using the potential difference and the time as axes. Similarly, based on the potential difference data between the third sensor 23 and the fourth sensor 24, the voltage waveform data V2 is generated (step S02).

Next, the selector 83b selects, from two pieces of voltage waveform data V1, V2, the data synchronized with the heart rate and having a high R-wave amplitude, thereby setting the selected data as the electrocardiographic waveform data VH (step S03).

Next, the arithmetic device 80 digitally filters the electrocardiographic waveform data VH to emphasize the waveform associated with a QRS-wave, and then, computes a peak interval at which the voltage (an R-wave potential) exceeding a set threshold is detected. Next, the arithmetic device 80 further calculates the number of detections per minute, the inverse of the peak interval being taken as an instantaneous heart rate (the number of heart beat per second). That is, the arithmetic device 80 calculates the heart rate by computing. Next, the arithmetic device 80 transmits the signals associated with the electrocardiographic waveform data VH and the heart rate to the display D, and then, the electrocardiographic waveform data VH and the heart rate are displayed on the display D (step S04).

Next, the arithmetic device 80 determines the presence or absence of the instruction of terminating heart rate measurement by a stop switch, and the like (step S05). With the instruction of terminating the heart rate measurement, the process is terminated. Without the instruction, steps S01 to S05 are repeated.

Second Embodiment of Sheet-Shaped Sensor 20

Figure 9:
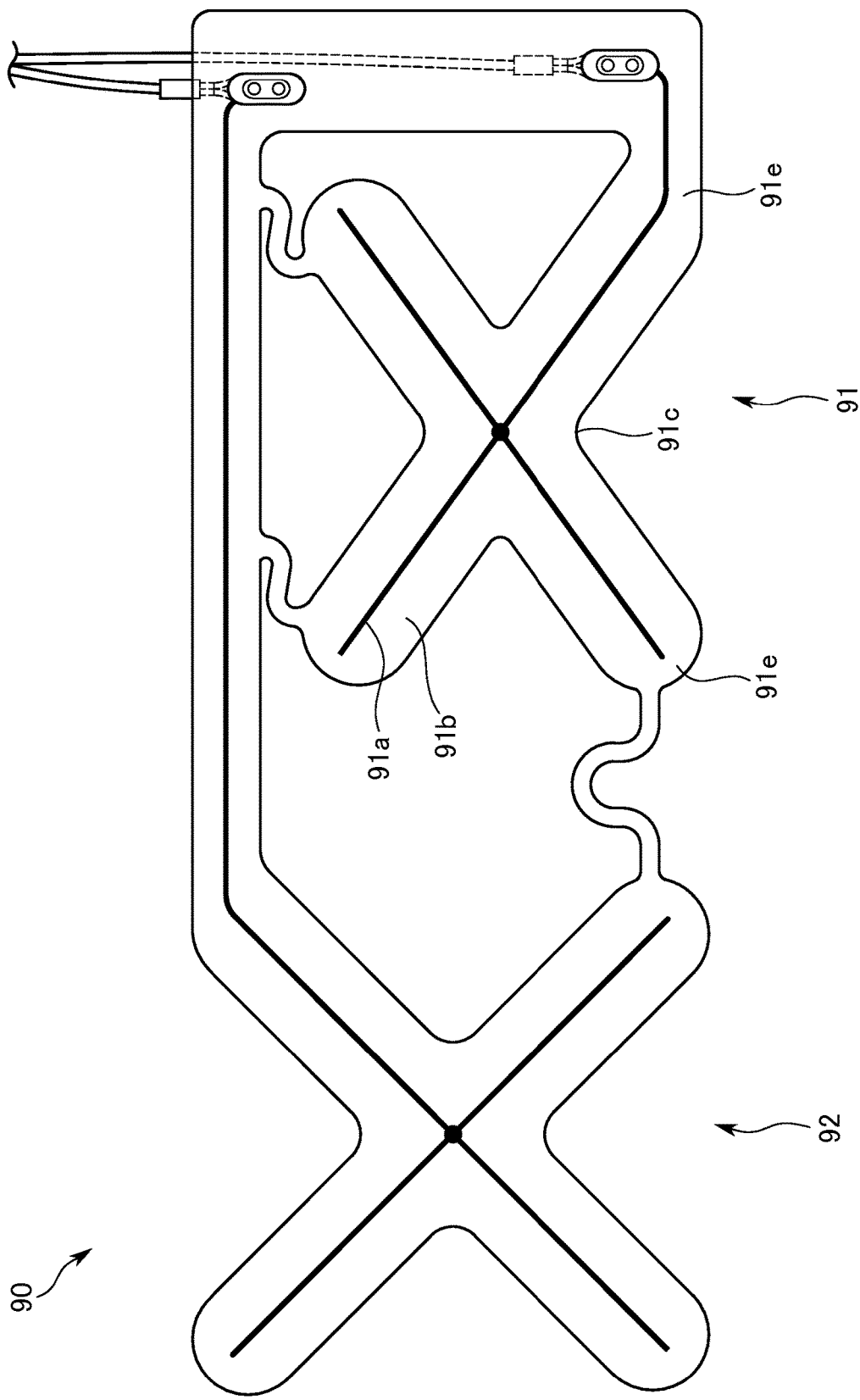
FIG. 9 is a front view illustrating a second embodiment of the sheet-shaped sensor.

Next, a sheet-shaped sensor 90 of a second embodiment will be described with reference to FIG. 9. Note that for the sake of clear explanation of feature differences, the contents overlapping with the sheet-shaped sensor 20 of the above-described embodiment will not be described below.

A first sensor 91 and a second sensor 92 configuring the sheet-shaped sensors 90 of the second embodiment are in a substantially X-shape, and as a feature thereof, are more downsized as compared to the shape of the sheet-shaped sensor 20.

A conductive line 91a configuring a sensor body of the first sensor 91 is bonded to the outer surface of a conductive sheet 91b along the substantially X-shape of the conductive sheet 91b.

The conductive sheet 91b includes, as a sensor overlap reduction section, four cutouts 91c formed in an outer peripheral portion of the conductive sheet 91b and extending opposite to the center along the outer peripheral portion.

Each cutout 91c is a substantially triangular cutout, and along the outer peripheral portion of the conductive sheet 91b, is formed wider with an increase in the distance from the center of the conductive sheet 91b.

Specifically, each cutout 91c extends from the center along the outer peripheral portion such that the width thereof increases toward the corners 91e positioned respectively on opposing sides relative to the center, supposing that four corners of the outer peripheral portion of the conductive sheet 91b positioned farthest from the center are the corners 91e. R is provided to each corner 91e.

The second sensor 92 and third and fourth sensors are in the same shape as that of the first sensor 91.

Third Embodiment of Sheet-Shaped Sensor 20

Figure 10:
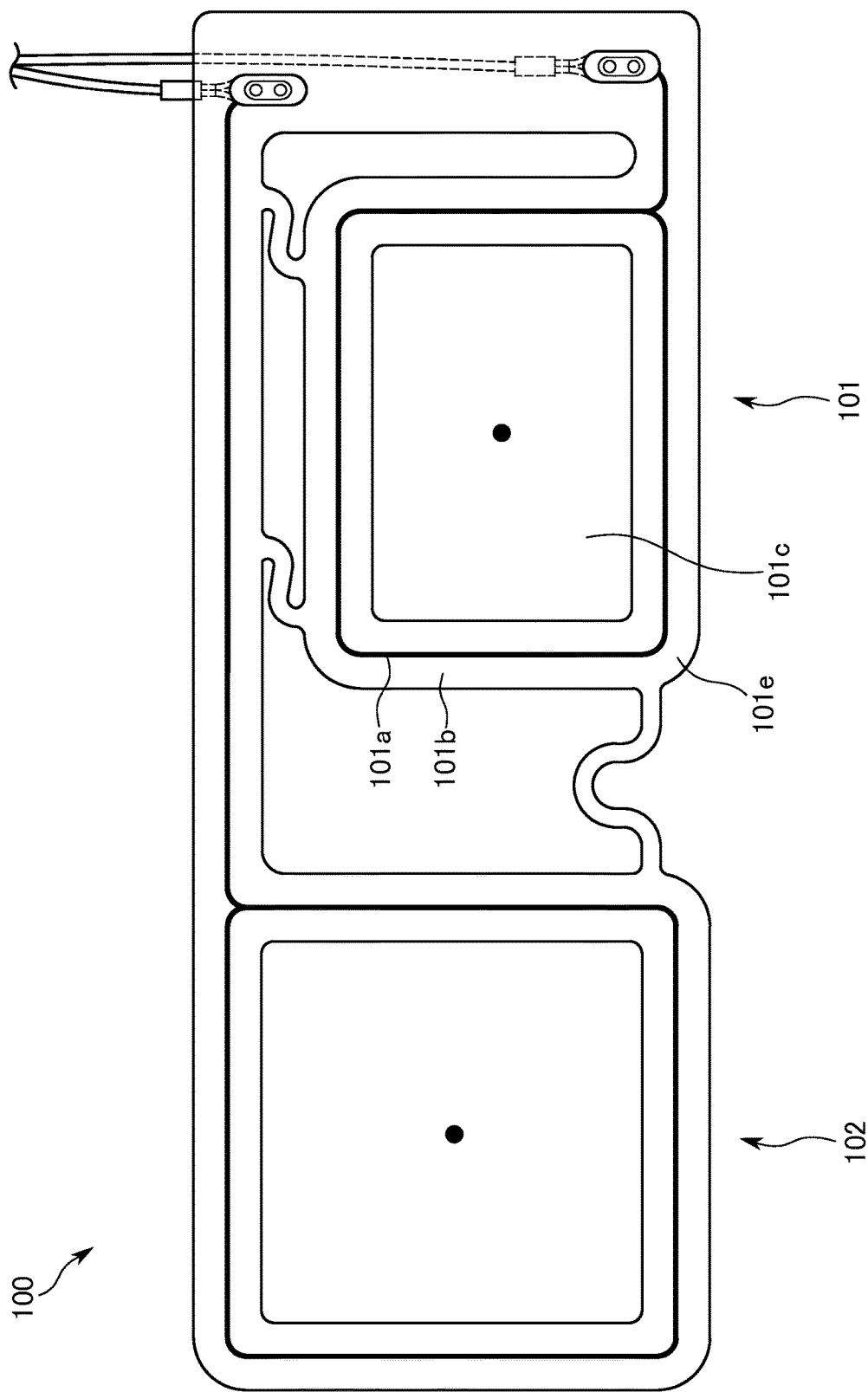
FIG. 10 is a front view illustrating a third embodiment of the sheet-shaped sensor.
Figure 11:
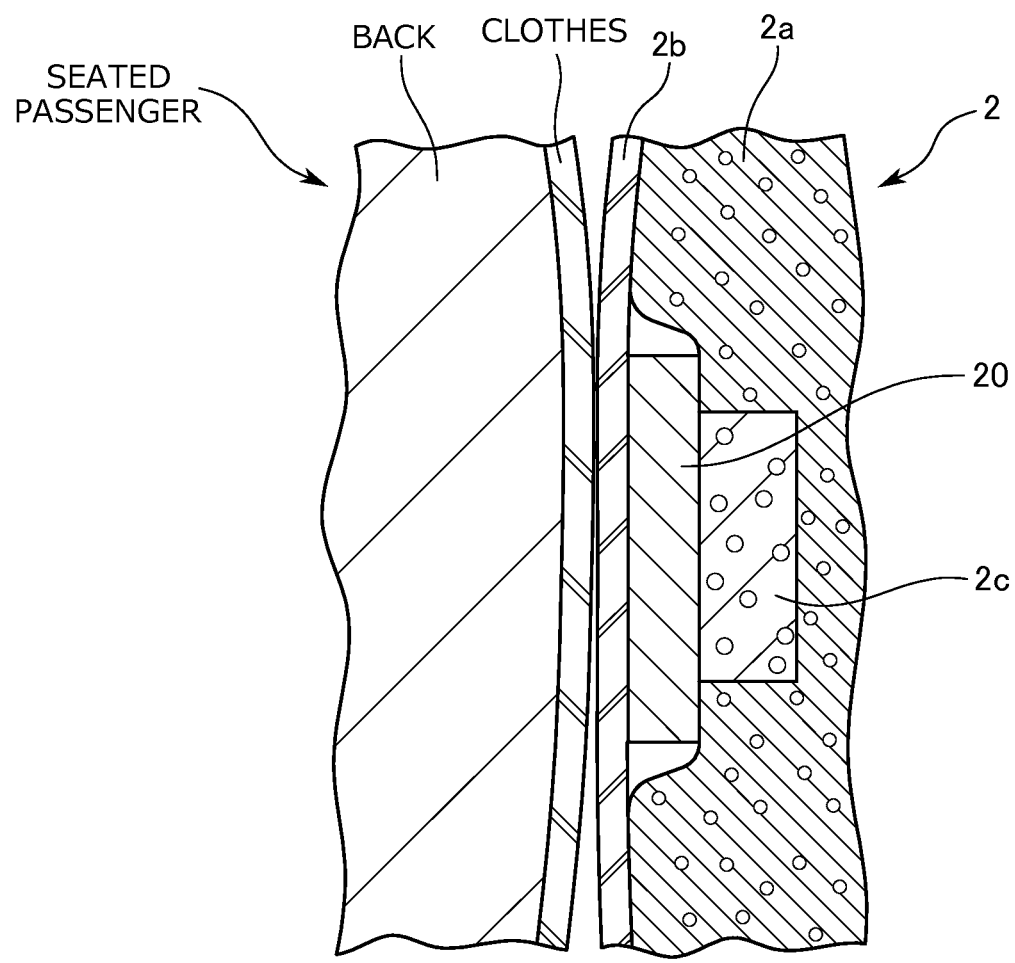
FIG. 11 is a partial longitudinal sectional view of a seat back illustrating arrangement of a deformable absorbing member.

Next, a sheet-shaped sensor 100 of a third embodiment will be described with reference to FIG. 10.

A first sensor 101 and a second sensor 102 configuring the sheet-shaped sensors 100 of the third embodiment are in a substantially rectangular frame shape as illustrated in the figure, and as a feature thereof, is more downsized as compared to the shape of the sheet-shaped sensor 20.

A conductive line 101*a* configuring a sensor body of the first sensor 101 is bonded to the outer surface of a conductive sheet 101*b* along the substantially rectangular frame shape of the conductive sheet 101*b*.

The conductive sheet 101*b* includes, as a sensor overlap reduction section, a cutout 101*c* formed by cutting out a substantially-rectangular center portion of the conductive sheet 101*b*, and a corner 101*e* provided with R.

The second sensor 102 and third and fourth sensors are in the same shape as that of the first sensor 101.

Other Embodiments

In the above-described embodiments, the vehicle seat S is configured such that the sheet-shaped sensor 20 includes, at the outer peripheral portion thereof, the cutouts as the sensor overlap reduction section, but the present invention is not limited to such a configuration. The sheet-shaped sensor 20 may be configured such that an opening or a cutout is formed in at least part of the sheet-shaped sensor 20.

The configuration may be employed in which the sensor overlap reduction section is provided in the seat back 2 to which the sheet-shaped sensors 20 are attached.

Specifically, the configuration may be employed in which part of the front side of the cushion pad 2*a* to which the sheet-shaped sensors 20 are attached is partially softened to provide the sensor overlap reduction section.

With such a configuration, when the seated passenger leans on the seat back 2, the sheet-shaped sensors 20 easily follow elastic deformation of the cushion pad 2*a*, and therefore, partial overlapping of the sheet-shaped sensor 20 can be reduced.

The configuration may be employed, in which a groove having a predetermined depth is, as another sensor overlap reduction section, formed in part of a portion of the front side of the cushion pad 2*a*, the sheet-shaped sensors 20 being attached to such a portion of the front side of the cushion pad 2*a*.

With such a configuration, when the seated passenger leans on the seat back 2, the sheet-shaped sensors 20 easily follow elastic deformation of the cushion pad 2*a*, and therefore, partial overlapping of the sheet-shaped sensor 20 can be reduced.

Note that the shape of the groove is optionally changeable according to the shape of the sheet-shaped sensor 20, and, for example, is a substantially petal-shaped cross-sectional shape, a substantially X-shaped cross-sectional shape, a substantially cross-shaped cross-sectional shape, or a substantially circular cross-sectional shape as viewed from the seat front side.

The configuration may be employed in which a well-known deformable absorbing member 2*c* is, as still another sensor overlap reduction section, disposed between the cushion pad 2*a* and each sheet-shaped sensor 20 at part of the front side of the cushion pad 2*a* to which the sheet-shaped sensors 20 are attached.

With such a configuration, when the seated passenger leans on the seat back 2, the sheet-shaped sensors 20 easily follow elastic deformation of the cushion pad 2*a*, and therefore, partial overlapping of the sheet-shaped sensor 20 can be reduced.

Note that, for example, an elastic member made of a cushion material or rubber can be used as the well-known deformable absorbing member 2*c*, and a material softer than the cushion pad 2*a* may be used. The shape of the deformable absorbing member 2*c* is optionally changeable according to the shape of the sheet-shaped sensor 20, and for example, is a substantially petal shape, a substantially X-shape, a substantially cross shape, or a substantially circular shape as viewed from the seat front side.

In the above-described embodiments, it has been described that the ground electrode 10 and the sheet-shaped sensors 20 are each formed of the conductive fabric tape, but the present invention is not limited to such a configuration. Such a material is optionally changeable as long as the material is a metal conductor having conductivity. Examples of the material include conductive fibers.

Each sheet-shaped sensor 20 includes the conductive line configuring the sensor body, and the conductive sheet for protecting the conductive line, but the present invention is not limited to such a configuration. The sheet-shaped sensor 20 may be formed only of the conductive sheet without the conductive line.

Note that, for example, gold paste, silver paste, or copper paste having a high conductivity can be used for the conductive line, and, for example, carbon paste resistive to oxidation and having conductivity can be used for the conductive sheet.

In the above-described embodiments, the sheet-shaped sensors 20 are arranged between the cushion pad 2*a* and the skin 2*b*, but the present invention is not limited to such a configuration. For example, the sheet-shaped sensors 20 may be attached to the skin 2*b*.

In the above-described embodiments, the number of sheet-shaped sensors 20 are four, but the number of sheet-shaped sensors 20 are not limited to four. The number of sheet-shaped sensors 20 may be optionally adjustable considering the balance between stability in potential difference detection and a manufacturing cost.

The second sensor 22 configuring the sheet-shaped sensor 20 has a larger size than that of the first sensor 21, and is disposed to protrude above the first sensor 21. However, the present invention is not limited to such a configuration. Conversely, the first sensor 21 may have a larger size than that of the second sensor 22, and may be disposed to protrude above the second sensor 22. Alternatively, the first sensor 21 and the second sensor 22 may have the same size.

Note that in the case where the first sensor 21 and the second sensor 22 are set to have the same size, the distribution cable 25 connected to the first sensor 21 may be disposed outside the first sensor 21 in the seat width direction at the seat back 2, and the distribution cable 25 connected to the second sensor 22 may be disposed outside the second sensor 22 in the seat width direction. Thus, the distribution cables 25 can be compactly arranged.

In the above-described embodiments, the heart rate measurement device 3 includes, as a component, the display D showing the electrocardiographic waveform, but may additionally include a vibration motor, a transmitter for generating an alarm, or a light emitter for emitting light, for maintaining the seated passenger in an awakened state.

Further, the vehicle seat S can be utilized for the purpose of monitoring a passenger having a heart problem. In this case, the display D may be disposed in such a position that a passenger(s) other than the passenger having the heart problem can monitor the working condition of the heart. In addition, a vibration motor may be provided in a seat other than the seat provided with the heart rate measurement device 3. When a decline in the function of the heart is detected, such a seat may vibrate to report to other passenger(s). Further, a typical communication section may be used to urgently report to a hospital, a fire department, or a police station.

In the above-described embodiments, the person with a height of 150 cm has been described as an example of the seated passenger assumed as being physically small, and the person with a height of 190 cm has been described as an example of the seated passenger assumed as being physically big. However, such an assumption is optional. For example, in the case of assuming only seating of an adult American or assuming only seating of a child, a reference physique may be set according to such assumption. Similar advantageous effects can be provided in the following manner. The positions of a plurality of the sheet-shaped sensors 20 are determined such that in the state in which a passenger with the reference physique is seated and faces forward of the seat back 2, the sheet-shaped sensors 20 sandwich the heart of the passenger.

In the above-described embodiments, the heart rate measurement device 3 which can measure the heart rate (the vital information) of the seated passenger based on the electric signal (the vital signal) associated with the biopotential of the seated passenger has been described as an example of the vital information measurement device. However, the present invention is not limited to the heart rate measurement device 3, and the heart rate measurement device 3 is changeable.

Examples include a respiration measurement device which includes sheet-shaped piezoelectric sensors configured to detect a change in expansion/contraction of the chest in association with respiration of the seated passenger and which can measure respiration, taken as the vital information of the seated passenger, based on the vital signals detected by the sheet-shaped piezoelectric sensors.

The examples further include a humidity measurement device which includes sheet-shaped humidity sensors (sheet-shaped capacitance sensors) configured to detect a change in humidity around the seated passenger in association with contact with the seated passenger and which can measure the humidity associated with the vital information of the seated passenger based on the vital signals detected by the sheet-shaped humidity sensors.

In the above-described embodiments, the vehicle seat used for automobiles has been described as a specific example, but the present invention is not limited to such a vehicle seat. The vehicle seat can be utilized not only as vehicle seats of trains and buses but also as vehicle seats of airplanes and ships.

The vital information measurement device may be applied not only to the vehicle seats but also to typical seats such as chairs, beds, and sofas. In addition to these seats, the vital information measurement device may be attached to attachment bodies contacting humans or animals, such as blankets, Japanese-style bedding, sheets, mats, and clothes. In this case, a subject may directly contact the sheet-shaped sensors, or may indirectly contact the sheet-shaped sensors via another member.

In the above-described embodiments, the vehicle seat including the vital information measurement device whose detection target is the seated passenger has been described, but is broadly applicable without limitation of the detection target.

For example, the detection target may be, in addition to the seated passenger, as seated animals, pets such as dogs and cats, and may be other animals such as cows and horses.

In the case of attaching the vital information measurement device to, for example, a blanket or clothes, measurement is not necessarily made with an subject being seated.

Embodiments of the vehicle seat S of the present invention have been mainly described.

Note that the above-described embodiments have been set forth merely as examples for the sake of easy understanding of the present invention, and are not intended to limit the present invention. Changes and modifications can be made to the present invention without departing from the idea of the present invention, and the present invention includes equivalents thereof.

In particular, the shape, arrangement, configuration of the sheet-shaped sensors 20 attached to the cushion pad 2a configuring the seat back 2 have been described merely as examples in the above-described embodiments, and are not intended to limit the present invention.

| TABLE OF REFERENCE NUMERALS | |
|---|---|
| S: | vehicle seat |
| 1: | seat cushion |
| 1a, 2a: | cushion pad |
| 1b, 2b: | skin |
| 2: | seat back (attachment body) |
| 2c: | deformable absorbing member |
| 3: | heart rate measurement device (vital information measurement device) |
| 10: | ground electrode |
| 20, 90, 100: | sheet-shaped sensor |
| 21, 91, 101: | first sensor |
| 21a, 22a, 91a, 101a: | conductive line |
| 21b, 22b, 91b, 101b: | conductive sheet |
| 21c, 22c: | first cutout |
| 21d, 22d: | second cutout |
| 21e, 91e, 101e: | corner |
| 22, 92, 102: | second sensor |
| 23: | third sensor |
| 24: | fourth sensor |
| 25: | distribution cable |
| 25a, 25b: | end |
| 26: | second sensor extension |
| 27: | sensor connection portion |
| 28: | cable housing recess |
| 29: | skin insertion groove |
| 29a: | skin insertion groove |
| 30: | instrumentation amplifier |
| 31, 32, 33: | operational amplifier |
| 40: | DC component removal circuit |
| 41: | capacitor |
| 50: | inverting amplifier |
| 60: | passband filter |
| 70: | A/D converter circuit |
| 80: | arithmetic device |
| 81: | CPU |
| 82: | RAM |
| 82a: | storage |
| 83: | ROM |
| 83a: | waveform generator |
| 83b: | selector |
| 91c: | cutout |
| 101c: | cutout |
| D: | display |
| V1, V2: | voltage waveform data |
| VH: | electrocardiographic waveform data |
| 120: | intersection point |

| TABLE OF REFERENCE NUMERALS | |
|---|---|
| 121: | bored hole |
| 122: | penetration hole |
| 123: | through hole |

The invention claimed is:

1. A vital information measurement device comprising:
a sheet-shaped sensor that is configured to detect a vital signal of a subject that is a human or an animal,
wherein:
the vital information measurement device is configured to measure vital information of the subject based on the vital signal detected by the sheet-shaped sensor,
the sheet-shaped sensor at least comprises a conductive line that forms a sensor body, and a conductive sheet fixing the conductive line,
the conductive line is disposed along an outer peripheral portion of the conductive sheet,
a sensor overlap reduction section configured to reduce partial overlapping of the sheet-shaped sensor when the subject directly or indirectly contacts the sheet-shaped sensor is provided in the sheet-shaped sensor, and
at least one or more cutouts are, as the sensor overlap reduction section, formed in the outer peripheral portion of the conductive sheet.

2. The vital information measurement device according to claim 1, wherein:
the sheet-shaped sensor is configured to detect an electric signal associated with a biopotential of the subject as the vital signal, and
the vital information measurement device further includes a central processing unit configured to measure a heart rate of the subject based on the electric signal detected by the sheet-shaped sensor.

3. The vital information measurement device according to claim 1, wherein the cutouts comprise:
a first cutout extending toward a center of the sheet-shaped sensor at the outer peripheral portion of the sheet-shaped sensor, and
a second cutout formed continuously from the first cutout and extending opposite to the center along the outer peripheral portion of the sheet-shaped sensor.

4. The vital information measurement device according to claim 1, wherein:
the conductive line is disposed along the cutouts provided in the outer peripheral portion of the conductive sheet.

5. The vital information measurement device according to claim 1, wherein:
the conductive line comprises a plurality of conductive lines, and
an intersection point at which the plurality of the conductive lines intersect each other is arranged opposed to one of the cutouts in a short-length direction or a long-length direction of the sheet-shaped sensor.

6. A vehicle seat comprising:
a seat back that is a backrest of the vehicle seat;
a seat cushion that is a seating portion of the vehicle seat; and
the vital information measurement device of claim 1,
wherein:
the vital information measurement device is attached to the seat back or to the seat cushion.

7. The vehicle seat according to claim 6, wherein:
the sheet-shaped sensor is attached to a cushion pad that forms the seat back,
a distribution cable is electrically connected to the sheet-shaped sensor and is configured to transmit the vital signal detected by the sheet-shaped sensor, a cable housing recess is formed in the cushion pad, and the distribution cable is housed in the cable housing recess.

8. The vehicle seat according to claim 7, wherein:
the seat back is configured such that the cushion pad is covered with a skin,
a skin insertion groove into which an end of the skin is inserted is formed in the cushion pad, and
the sheet-shaped sensor is disposed in a position other than a part of the cushion pad formed with the skin insertion groove.

9. The vehicle seat according to claim 8, wherein the sheet-shaped sensor is disposed along the skin insertion groove.

10. A vehicle seat comprising:
a skin, a cushion pad and the vital information measurement device of claim 1, wherein:
the vital information measurement device is attached to the cushion pad,
the vital information measurement device includes a distribution cable electrically connected to the sheet-shaped sensor and configured to transmit the vital signal detected by the sheet-shaped sensor,
a skin insertion groove into which an end of the skin is inserted is formed in the cushion pad,
a through hole through which the distribution cable passes is formed in the cushion pad, and
the sheet-shaped sensor and the through hole are configured to avoid the skin insertion groove.

* * * * *